(12) United States Patent
Karlsson et al.

(10) Patent No.: US 9,167,997 B2
(45) Date of Patent: Oct. 27, 2015

(54) SELF-FLOWING MEASURING SYSTEM

(75) Inventors: Anton Karlsson, Enskede (SE); Henrik Falkén, Lidingö (SE); Gabriel Österdahl, Solna (SE); Jan Liska, Stockholm (SE)

(73) Assignee: Maquet Critical Care AB, Solna (SE)

( * ) Notice: Subject to any disclaimer, the term of this patent is extended or adjusted under 35 U.S.C. 154(b) by 624 days.

(21) Appl. No.: 13/509,939

(22) PCT Filed: Nov. 16, 2010

(86) PCT No.: PCT/SE2010/051256
§ 371 (c)(1),
(2), (4) Date: Aug. 2, 2012

(87) PCT Pub. No.: WO2011/059397
PCT Pub. Date: May 19, 2011

(65) Prior Publication Data
US 2012/0289795 A1    Nov. 15, 2012

Related U.S. Application Data

(60) Provisional application No. 61/261,449, filed on Nov. 16, 2009.

(30) Foreign Application Priority Data

Nov. 16, 2009   (SE) ...................................... 0901453

(51) Int. Cl.
*A61B 5/145* (2006.01)
*A61B 5/155* (2006.01)
*A61B 5/00* (2006.01)

(52) U.S. Cl.
CPC ............... *A61B 5/155* (2013.01); *A61B 5/1427* (2013.01); *A61B 5/14503* (2013.01);
(Continued)

(58) Field of Classification Search
CPC .. A61B 5/155; A61B 5/1427; A61B 5/14503; A61B 5/14528; A61B 5/14532; A61B 5/14542; A61B 5/412; A61B 5/686; A61B 5/6876

USPC ................. 600/309, 364, 365, 573, 582, 583; 29/428
See application file for complete search history.

(56) References Cited

U.S. PATENT DOCUMENTS

| 3,658,053 A | 4/1972 | Fergusson et al. |
|---|---|---|
| 3,893,448 A | 7/1975 | Brantigan |

(Continued)

FOREIGN PATENT DOCUMENTS

| EP | 0539625 A1 | 5/1993 |
|---|---|---|
| GB | 2003388 A | 3/1979 |
| GB | 2017907 A | 10/1979 |

OTHER PUBLICATIONS

Third Party Observation from corresponding EP 2010830290.2 dated Feb. 26, 2013.

(Continued)

*Primary Examiner* — Eric Winakur
(74) *Attorney, Agent, or Firm* — Porter Wright Morris & Arthur LLP

(57) ABSTRACT

The invention relates to a method and arrangement for continuously measuring substances in a pressurised body fluid. A probe (202) for enabling continuous measurement of the concentration of one or more substances in a pressurized body fluid is provided. The probe is adapted to be inserted into the pressurized body fluid, and comprises an interface and an outlet lumen. Furthermore, the probe is configured so that a continuous and spontaneous fluid flow is established from the body fluid through the interface to the outlet lumen. The fluid flow from the outlet may be analyzed by a sensor.

25 Claims, 4 Drawing Sheets

(52) U.S. Cl.
CPC ............ *A61B 5/14528* (2013.01); *A61B 5/412* (2013.01); *A61B 5/686* (2013.01); *A61B 5/14532* (2013.01); *A61B 5/14542* (2013.01); *A61B 5/6876* (2013.01); *Y10T 29/49826* (2015.01)

(56) References Cited

U.S. PATENT DOCUMENTS

| | | |
|---|---|---|
| 4,340,615 A | 7/1982 | Goodwin et al. |
| 4,534,825 A | 8/1985 | Koning |
| 4,685,463 A | 8/1987 | Williams |
| 4,979,509 A | 12/1990 | Hakky |
| 5,078,135 A | 1/1992 | Caprioli |
| 6,459,917 B1 * | 10/2002 | Gowda et al. ................ 600/345 |
| 2003/0236454 A1 | 12/2003 | Liska et al. |
| 2004/0191848 A1 | 9/2004 | Hoss et al. |
| 2005/0020890 A1 | 1/2005 | Schregel |

OTHER PUBLICATIONS

Extended European Search Report from corresponding EP 2010830290.2 dated Aug. 2, 2013.

* cited by examiner

SELF-FLOWING MEASURING SYSTEM

RELATED APPLICATIONS

The present application is a 371 of PCT/SE2010/051256 filed Nov. 16,2010 and claims priority under 35 U.S.C. 119 U.S. application Ser. No. 61/261,449 filed Nov. 16, 2009.

TECHNICAL FIELD

The present invention generally relates to continuous measurement of substances present in body fluid.

In particular, the present invention can be used when measuring substances that are indicators of pathological conditions and the sampling probe may be placed in a blood vessel.

BACKGROUND

It is known that certain substances which may be present in the body can function as indicators for various pathological conditions in the body. Such substances are hereafter called indicator substances. Examples of indicator substances are glucose, lactate, pyruvate, glycerol, glutamate, and glutamine, cytokines and heart specific enzymes. Pathological conditions that may be indicated or detected, or as well forecasted, include ischemia, hypoglycemia, hyperglycemia, sepsis, cell membrane damage or lipolysis, vasospasms, metabolic disorders and inflammatory disorders. By measuring indicator substances, pathological conditions may be detected before they lead to clinical signs. It may even be possible to detect processes or conditions that eventually may lead to a pathological condition. In many cases it would be advantageous to have the possibility to measure the concentration of indicator substances directly in a blood stream, or in tissue fluid. However, until now there have not existed any systems suitable for clinical use for continuous measurement of indicator substances. Systems known from the background art all have different drawbacks. Examples of common drawbacks in background art systems are that the measurement delay is extensive and that those systems have measured phenomena that are the result of a pathological condition, e.g. ischemia. This is clearly disadvantageous. With measurement delay is meant the time that passes from the moment that a sample is taken until the moment that a measurement value relating to this sample is obtained. Also, in background art systems measurement values can often only be obtained with relatively extended time periods between each measurement value, e.g. if sample fluid is collected in micro-vials. In another system, according to prior art, blood samples are drawn from a patient before being analysed with a blood gas analyser. In a further system, also according to prior art, a microdialysis probe provided with a semi-permeable membrane is inserted into a vein of a patient. A perfusion fluid (perfusate) is pumped into an inlet lumen before entering a microdialysis chamber on the inside of the membrane. The perfusate absorbs substances in the blood through the membrane and passes into an outlet lumen of the probe and then flows through a sensor where the substances are measured.

U.S. Pat. No. 5,078,135 describes a measuring system where a drug is administered to a rat and where a microdialysis probe is placed in the vein of the rat. Mass spectrometry is used to batchwise analyse the dialysate for obtaining pharmacokinetic data.

US-A1-2004/0191848 describes a system for measuring the concentration of glucose in tissue fluid. The system uses a microdialysis probe which is fed with a perfusate already containing glucose. The concentration of glucose in the perfusate is controlled using self-adaptive control.

In view of the prior art, there is a need for a more reliable and accurate measuring system that can be used in monitoring the condition of a critical care patient.

DESCRIPTION OF THE INVENTION

It is an object of the present invention to provide a measuring system that is improved with respect to the background art. Further, it is an object of the present invention to provide a mechanism for measuring the current amount of substances in body fluid, with relevant accuracy and without introducing much delay. It is also an object of the invention to provide a measuring probe which is simplified in construction and operable without pumps and other accessories normally associated with, for instance, microdialysis equipment. These objects may be met by an arrangement and a method according to the attached independent claims.

Briefly described, the present invention provides a solution for enabling a less complex and more exact system for measuring of substances in a body fluid.

The term "analysate" is used throughout this description to define an outflow from the probe transported to the sensor and then subsequently analysed.

The term "ultrafiltration" refers to a membrane filtration in which pressure forces a liquid against a semipermeable membrane. Suspended solids and solutes of high molecular weight are retained, while water and low molecular weight solutes pass through the membrane.

The term "probe" refers to a catheter or probe suitable to be inserted into a living body. The term "membrane" refers to a microporous semipermeable structure.

The term "flow lumen" refers to a channel inside the probe that actively carries a liquid to and/or from the membrane of a probe.

The terms "spontaneous flow or spontaneous fluid flow" used in the following section means that the flow is generated from the pressurized body fluid entirely without any energized device, such as pumps. In other terms no external or extracorporeal force is used to generate a flow through the membrane and into the flow lumen.

In general terms the present invention relates to a probe which is adapted to be inserted into a pressurized body fluid and to receive a fluid flow that is subsequently analyzed. The probe comprises an essentially cylindrical elongated body with a proximal part, a distal part and at least one chamber part covered by a membrane, The chamber part is in fluid connection with a flow lumen The probe body is provided with one single flow lumen for transporting a spontaneous flow of fluid, continuously obtained from the body fluid through the membrane, from the chamber to the proximal part of the probe for subsequent measurement of the concentration of one or more substances present in the pressurized body fluid. In the present context, the term "one single flow lumen" means that the probe is devoid of any other flow lumen or comprising one or more inoperable flow lumens, for example conventional flow lumens extending from the chamber part to the proximal part which are plugged. The probe further preferably comprises a through-hole extending from the chamber to the single flow lumen in order to admit passage of fluid flow. In one embodiment, the chamber is essentially annular in cross-section and extends laterally along the probe body with a generally cylindrical shape and communicates with single flow lumen with a single through-hole so that fluid communication is established.

It is an important part of the invention that the membrane is selected with respect to the pressure in the body fluid, so as to accomplish ultrafiltration and thereby generate a spontaneous fluid flow through the membrane and in the lumen of the probe in the range of 1 to 50 µl/min. The pressurized body fluid will have a mean pressure of about 2-250 mmHg. In the arteries a systolic pressure of about 80-200 mmHg and a diastolic pressure of about 50-120 mmHg, and in the veins the pressure is in the range of 2-8 mmHg. In order to accomplish ultrafiltration and the fluid flow in the meaning of the present invention, a membrane is selected with suitable liquid permeability, membrane area, thickness, as well as a suitable pore size and surface roughness adapted to face the body fluid.

Generally, the liquid permeability (Lp) of the membranes applicable with the present invention vary from between about 1 to $150*10^{-4}$ cm/(bar*s). For an arterial probe, a suitable liquid permeability is about 5 to $50*10^{-4}$ cm/(bar*s) in order to obtain a suitable fluid flow rate in the probe from about 2 to 10 µl/min. It lies within the concept of the present invention to select appropriate flow rates in the probe by selecting suitable membrane parameters. On one hand a too low flow rate will generate unacceptable delay times from the pick-up of the flow through the membrane to the moment the carried analytes reach a sensor or a sampling function. On the other hand a too high flow rate may risk causing clinical complications by draining the body site from fluid and generate unnecessary waste. A preferred surface area of membranes with the probe is within the range of 5 to 500 $mm^2$, more preferably of about 30 to 200 $mm^2$ and the membrane has a thickness of 30 to 80 µm.

The probes can generally be adapted to be inserted into a blood vessel and have a length of about 5 to 60 cm, while the single flow lumen has an internal diameter of about 0.05 to 0.3 mm, preferably of about 0.15 mm. An especially suitable such probe for insertion into an artery, has a membrane with a liquid permeability of $5-50*10^{-4}$ cm/(bar*s), a membrane area of 30 to 200 $mm^2$ and a thickness of 30 to 80 µm Probes especially suitable for arterial applications include an approximately 50-250 mm long catheter having an external diameter of about 0.7-1.4 mm, an internal flow lumen of about 0.1-0.3 mm, a membrane of a hollow-fibre type with an outer diameter of about 0.9-1.6 mm and a wall thickness of about 30-80 µm, a surface area of about 30-100 $mm^2$ and a liquid permeability of about $20-50*10^{-4}$ cm/(bar*s). It is understood that the above values are approximate and may be adapted depending on in which artery the probe is to be placed.

A working embodiment of a probe for an arterial application includes an approximately 70 mm long catheter having an external diameter of about 1.1 mm, an internal flow lumen of about 0.15 mm, a membrane hollow-fibre with an outer diameter of about 1.3 mm and a wall thickness of about 50 µm, a surface area of about 60 $mm^2$ and a liquid permeability of about $40*10^{-4}$ cm/(bar*s).

The probes can be further adapted for continuous measurement by including sensing functions, or adapted to collect at least one sample for other types of analyze. The probes can also include additional lumens for other conventional purposes than fluid transport, for example admitting direct access (without any membrane) to the pressurized body fluid.

In another aspect, the invention relates to a method of manufacturing a probe for insertion into a pressurized body fluid that ascertains a continuous fluid flow through a membrane contacting the body fluid flow lumen extending from a distal to a proximal part of the probe for sampling or sensing of one or more compounds in the body fluid. The method typically comprises the steps of providing an elongated probe body having an internal flow lumen connected to a chamber coverable with a membrane; estimating the pressure range of the body fluid in a selected body site; selecting a membrane that at the estimated pressure range of body fluid provides a spontaneous fluid flow of about 1-50 µl/min; and finally attaching the membrane to sealingly cover the probe chamber. The membrane is selected in accordance with what have been discussed above regarding consideration to the pressure range of the body fluid with respect to the mentioned important membrane characteristics in order to obtain a desired flow rate in the probe. The elongated probe body can be provided with a single flow internal lumen connected to the chamber and a single through-hole connecting the chamber and the lumen, or alternatively there are one or more additional internal flow lumens made inoperable for fluid transport, for example by a plug. The method can involve selecting a membrane from a kit of membranes, wherein each membrane has a liquid permeability, area and adapted to a pressure range of the body fluid.

In yet another aspect, the present invention relates to a method for measuring the concentration of one or more substances in a pressurized body fluid with a pressure of about 2 to 250 mmHg. The method comprises the steps of inserting a probe as described above in a body site containing the pressurized body fluid; establishing a spontaneous fluid flow through a membrane of the probe and transporting at least a part of said fluid flow to a sensor adjacent to the probe outlet or to sampling function associated with the probe and detecting continuously a substance present in the body fluid or analyzing the collected samples.

According to a still further aspect, a self-flowing system for measuring the concentration of one or more substances or analytes in a pressurized body fluid is provided. The system comprises the above described probe, and a sensor adapted to receive and analyze the fluid. The sensor is connected to the outlet lumen of the probe described above. The sensor continuously provides data to monitoring means. The above described method and arrangements may be used for continuous measurement of the current amount of substance(s) in a pressurised body fluid, with relevant accuracy and reasonable response times. Further features and benefits of the present invention will become apparent from the detailed description.

BRIEF DESCRIPTION OF THE DRAWINGS

The present invention will now be described in more detail by means of exemplary embodiments and with reference to the accompanying drawings, in which.

DETAILED DESCRIPTION

Before the system described herein is described in detail, it is to be understood that this system is not limited to the particular component parts of the devices described or steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" also include plural referents unless the context clearly dictates otherwise. Thus, for example, reference to "a substance" includes more than one such substance, and the like.

Figure 1:
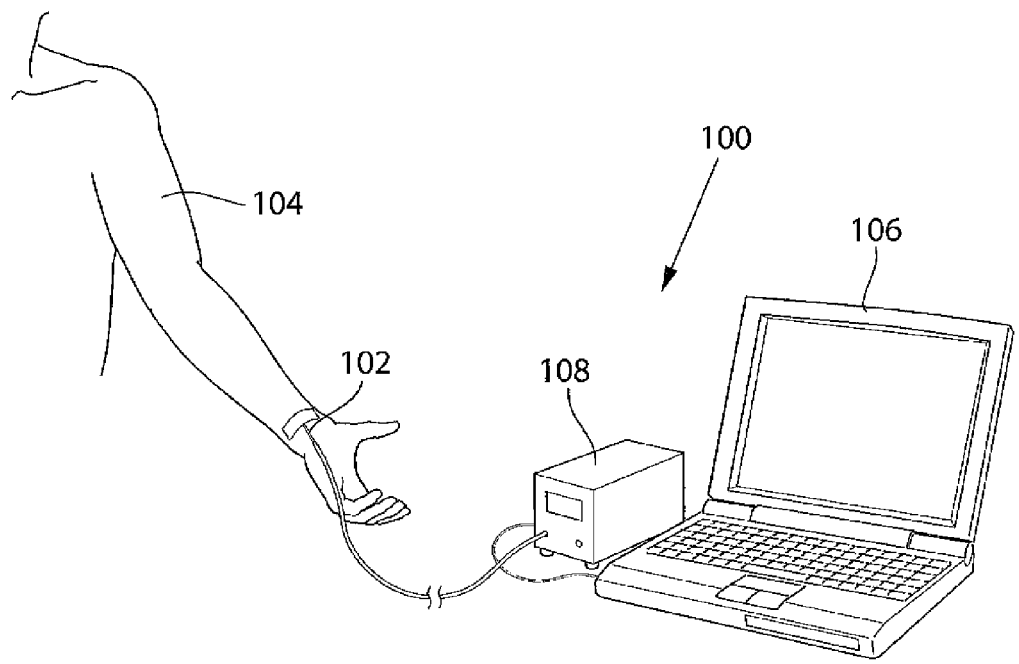
FIG. 1 is a basic overview illustrating a scenario where a substance in a pressurised body fluid y is analysed, in accordance with one embodiment.

With reference to FIG. 1, a self-flowing measuring system 100 for continuous measurement of substances in a pressurised body fluid, according to an embodiment, will now be described.

A measuring probe 102 is inserted into a pressurised body fluid of a patient 104. Typically, the pressurised body fluid is the blood flowing in a suitable artery of the patient, e.g. the radial artery. However, the invention is not limited to measurements of substances in arteries; a skilled person may easily modify the method to be able to perform measurements of substances in any other pressurised body fluid, e.g. any pressurised artery or vein, in the manner described. Typically, the pressure of the body fluid will be in the range of 2 to 250 mmHg.

Figure 2:
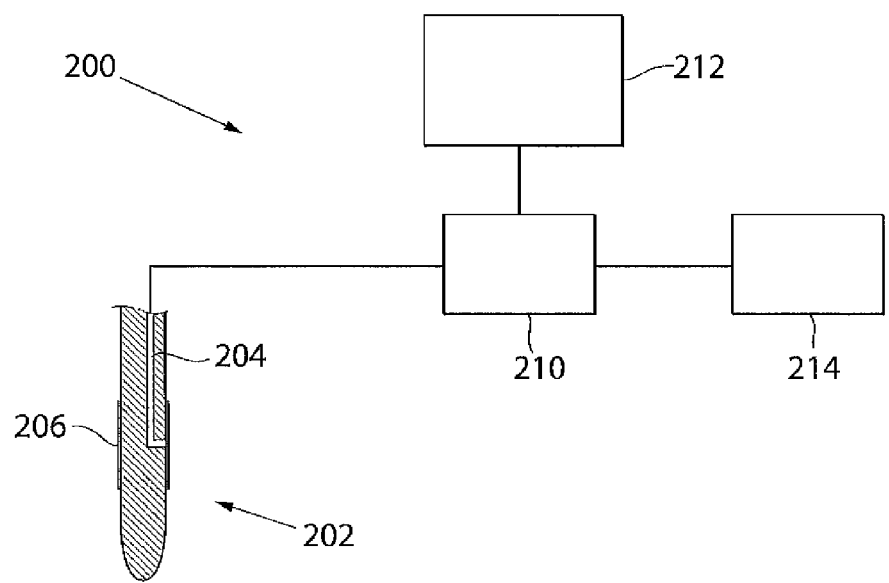
FIG. 2 is a block diagram illustrating a system for analysing a substance in a pressurized body fluid, in accordance with another embodiment.

The probe 102 is connected to a monitoring means 106, via a sensor 108. The probe 102, the monitoring means 106, and the sensor 108 will be described in more detail in embodiments below. According to this embodiment, the length of the probe will be 5-60 cm. It should be noted that, even if the above described self-flowing system is adapted to be applied for continuous measurements, a skilled person will easily realise how to modify the system, e.g. to enable collection of samples for analysis in vitro. With reference to FIG. 2, showing a block diagram, a self-flowing system 200 for measuring the concentration of one or more substances or analytes, according to another embodiment will now be described. The self-flowing system 200 comprises a probe 202, a sensor 210, a monitoring means 212, and a waste container 214. The probe 202 is inserted into a suitable pressurised body fluid of a patient (not shown). The probe 202 further comprises an outlet lumen 204, one or more through-holes (not shown) connecting the outer surface of the probe 202 with the outlet lumen 204, and an interface 206 covering the through-hole(s). In this embodiment, the membrane has a very smooth surface on the part of the membrane being in contact with the body fluid. The sensor 210 is situated adjacent to the proximal end of the outlet lumen 204, and detects the concentration of at least one substance from a pressurised body fluid, when the substance passes from the patient through the membrane via the outlet lumen 204 and into the sensor 210. However, the invention is not limited thereto; the sensor 210 may alternatively be situated in the outlet lumen 204. According to this embodiment, the sensor 210 is connected to the proximal end of the outlet lumen 204 of the probe 202, and conveys data regarding the detected concentration to the monitoring means 212. The sensor 210 and the monitoring means 212 may be connected wirelessly or by a direct cable. Such monitoring means can be realised as a computer monitor, a display device, etc. Furthermore, the sensor 210 is a flow-through sensor and the fluid flow passing the sensor 210 is collected in the waste container 214. The collection of fluid flow enables further analyses of the fluid flow, e.g. spectrophotometric analysis in vitro. It should also be noted that the invention is not limited to the above described embodiments of self-flowing systems 100, 200, a skilled person may easily realise how to modify the self-flowing system 100, 200, e.g. by omitting the waste container 214, by selecting an alternative sensor type and/or another type of monitoring device, etc.

Figure 3:
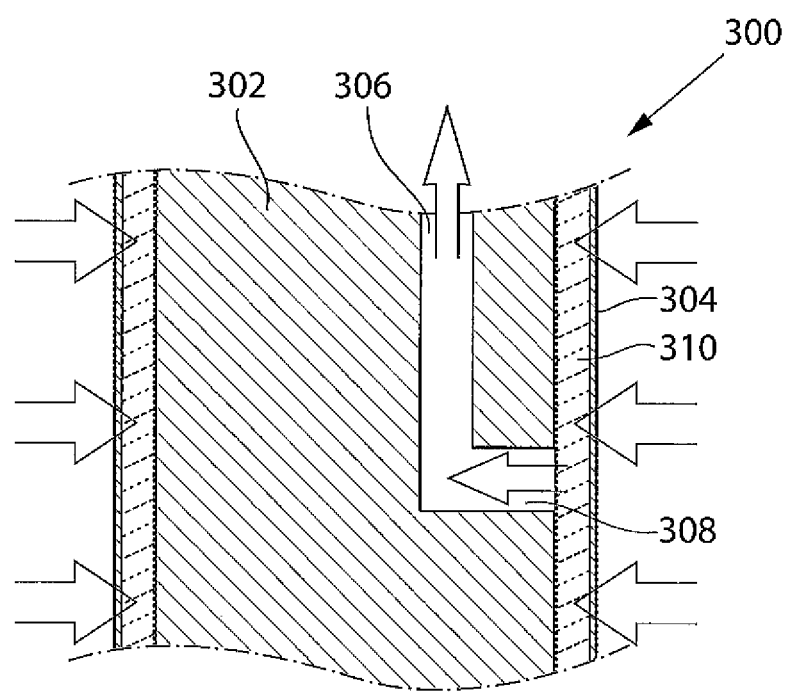
FIG. 3 is a schematic part of a cross-sectional view longitudinal through a probe, in accordance with a further embodiment.

With reference to FIG. 3, showing a part of a cross-sectional longitudinal view through a probe 300, the design of the probe 300 according to a specific embodiment will now be described. The probe 300 comprises a body 302 and a membrane 304. The probe body 302 is partly provided with an outlet lumen 306, and at least one through-hole 308 connecting the outside of the probe body 302 with the outlet lumen 306. The probe body 302 is covered with the membrane 304. The semipermeable membrane 304 is selected with special characteristics regarding the liquid permeability Lp, the surface area, as well as -the pores sizes and the surface roughness facing the pressurized body fluid. According to this embodiment, the membrane is a PAES hollow-fibre membrane from Gambro, with an outer diameter of 1.55 mm and a wall thickness of about 50 μm. The liquid permeability Lp, also called hydraulic permeability, hydraulic conductivity or the filtration coefficient (Kf), is $6.6*10^{-4}$ cm/(bar*s), the surface area of the membrane is about 195 $mm^2$. Regarding surface roughness, pore sizes and other overall membrane characteristics, suitable membranes, for this application and other applications discussed with the present invention, are found in WO 2008/046779 (Gambro Lundia AB). The through-hole 308 is situated at the distal part of the probe body 302. The outlet lumen 306 transports a flow of a liquid comprising substance(s) from a body fluid, which flows through the membrane via the through-hole 308 into the distal end of the outlet lumen 306 and then to the proximal end of the outlet lumen 306. A skilled person realises easily how to manufacture the through-hole 308. In this embodiment, a cut is made in the outside of the probe body 302, connecting the outside of the probe body 302 with the outlet lumen 306. The manufacturing of the outlet lumen 306 may, for instance, be performed by forming a longitudinal lumen through the probe body 302 during extrusion, and then providing a stopper (not shown) in the outlet lumen 306 distally from the through-hole 308. The stopper prevents the outlet flow from flowing distally in the outlet lumen 306. Alternatively, the interface 304 will cover just the through-hole(s) 308 of the probe body 302, instead of surrounding the complete probe body 302. Furthermore, a chamber 310 may be created between the interface 304 and the probe body 302.

Figure 4A:
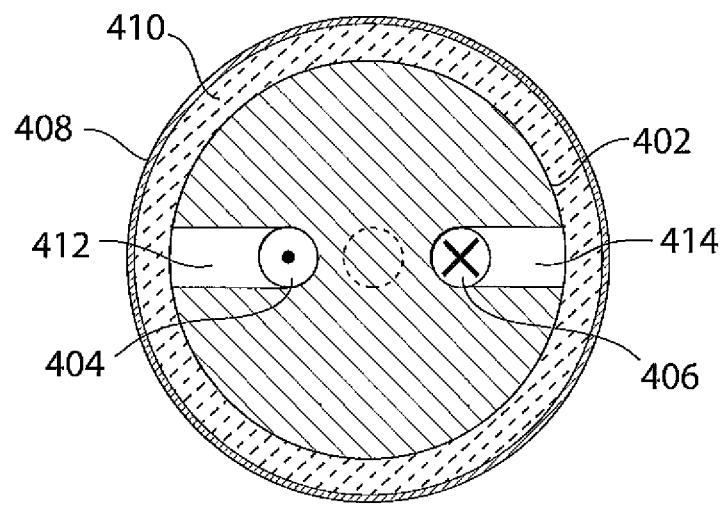
FIG. 4a is a schematic cross-sectional view transverse a probe, according to an example.

With reference to FIG. 4a, showing a transversal cross-sectional view, seen from the distal side, a conventional microdialysis probe 400 is described. The microdialysis probe 400 comprises a probe body 402, an inlet lumen 404, an outlet lumen 406, a membrane 408, a microdialysis chamber 410, and through-holes 412, 414. The microdialysis probe 400 is adapted to be inserted into a body fluid of a patient, e.g. in an artery or vein.

The inlet lumen 404 is provided in the probe body 402 and transports a perfusate to the microdialysis chamber 410 via the through-hole 412, which connects the inlet lumen 404 with the microdialysis chamber 410. Typically, the perfusate is pumped into the proximal end of the inlet lumen 404. In the microdialysis chamber 410, the perfusate absorbs substances from the body fluid surrounding the microdialysis probe 400, through the membrane 408. The perfusate, which have been absorbing substances, will be denoted as analysate. The through-hole 414 is provided in the probe body 402 and transports the analysate from the microdialysis chamber 410 to the outlet lumen 406, to be transported to the proximal end of the probe 400. Adjacent to the proximal end of the probe 400, a sensor (not shown) may be provided, adapted to analyse the analysate.

Figure 4B:
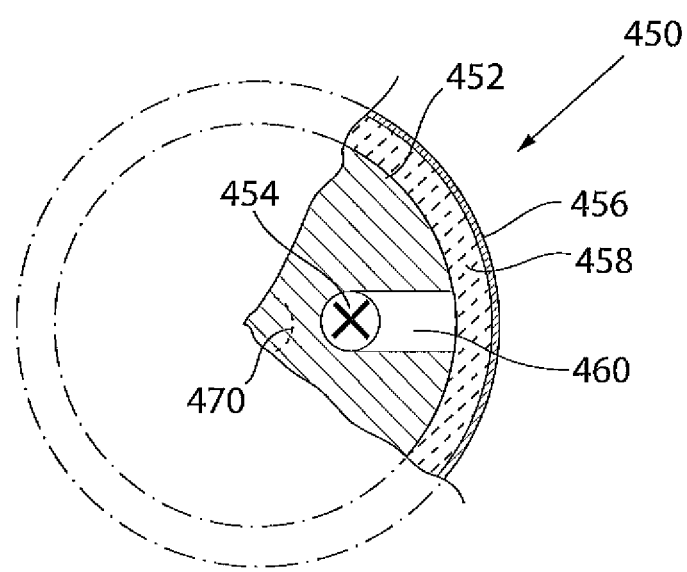
FIG. 4b is a part of a schematic cross-sectional view transverse a probe, in accordance with another embodiment.

With reference to FIG. 4b, showing a transversal cross-sectional view, seen from the distal side, a self-flowing probe 450 according to an embodiment will now be described. The self-flowing probe 450 comprises a probe body 452, an outlet lumen 454, a membrane 456, at least one through-hole 460. The self-flowing probe 450 is adapted to be inserted into a pressurised body fluid of a patient, e.g. in a suitable artery or vein. The probe body 452 is covered with the membrane 456, at least where the through-hole is located. The self-flowing probe 452 is adapted to absorb substances and liquid from the surrounding body fluid through the membrane 456, and transport via the through-hole 460 to the outlet lumen 454. The outlet lumen 454 is adapted to further transport the substances and liquid to its proximal, e.g. to be analysed. The analysis may be performed by a flow-through sensor (not shown) at the proximal end of the self-flowing probe 450 and/or by collecting the analysate and analyse it in vitro. How the analysis is performed can easily be realised by a skilled person, and is therefore not necessary to be further discussed here.

Alternatively, the self-flowing probe 450 comprises a chamber 458, defining a space between the membrane and the probe body 452. The probe body 452 may further comprise additional components or means for providing functionality to the probe 450. For instance, an additional lumen 470 to facilitate insertion, measure blood pressure, and draw blood samples may be provided in the probe body 452.

An advantage with the self-flowing probe 450 is that no perfusate needs to be supplied to the probe 450. Consequently, no inlet lumen needs to be provided in the self-flowing probe 450, and the design of the self-flowing probe 450 therefore is simplified. Moreover, the probe can be designed with a smaller diameter, or can contain additional components without increasing the diameter of the probe. Additionally, because a system applying the above described self-flowing probe 450 is self-flowing, the system does not need to apply a pump and syringe for supplying perfusate, which makes the system less complex.

Figure 5:
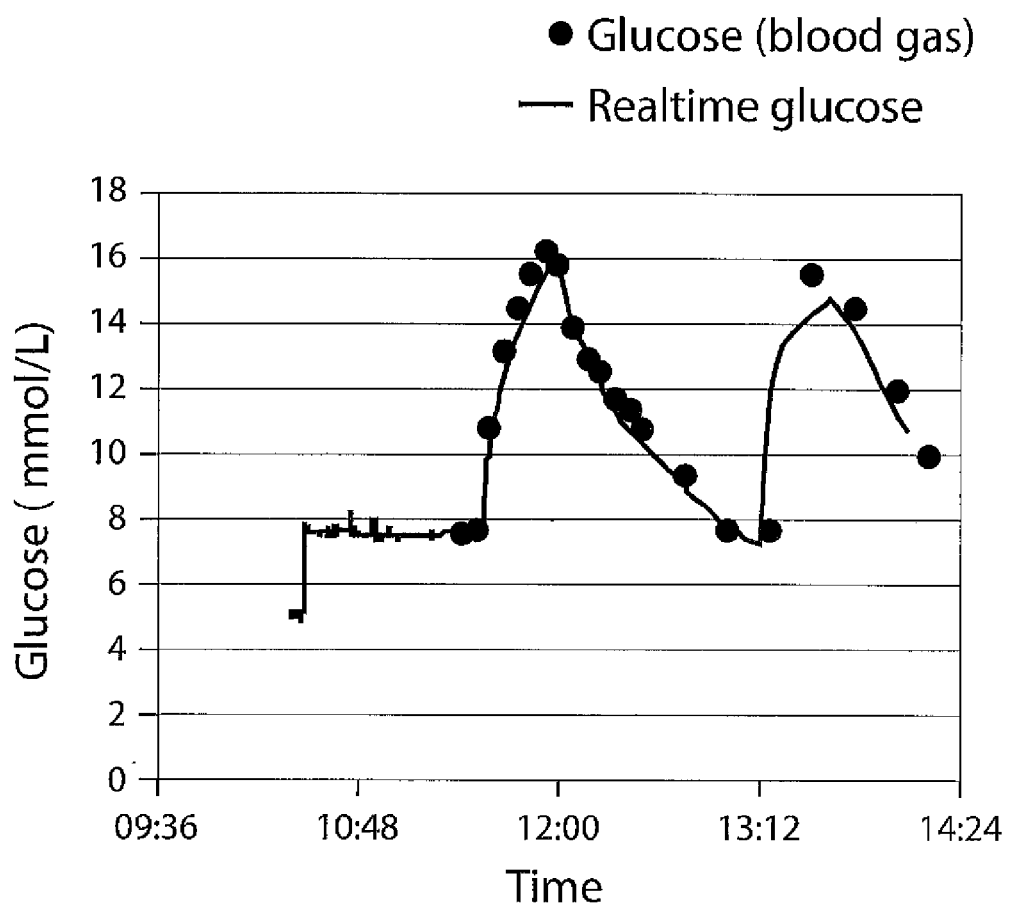
FIG. 5 demonstrates results with a system according to the present invention with the probe placed in arterial blood of a test animal.

With reference to FIG. 5, a comparison between a real-time analysis and a blood gas analysis will now be described. A comparison test was made with a self-flowing system, described in an embodiment above. A self-flowing probe as described with FIG. 3 was inserted into a femoral artery of a pig. The diagram comprises two graphs; a first graph indicated by a line illustrates the result of an analysis of glucose performed by applying a flow-through sensor at the proximal end of the self-flowing probe, and analysing the analysate flowing through the sensor. A second graph indicated by black dots illustrates the result of a blood gas analysis of the blood in the femoral artery of the pig. The system will always provide a fluid flow, having the correct concentration of analytes, to the sensor. The liquid and the analytes present in the surrounding body fluid will spontaneously be forced through the membrane. The rate at which the liquid and the analytes will pass depends mostly on the surrounding pressure as well as the liquid permeability and the surface area of the membrane. At a higher pressure as in an artery a lower liquid permeability is suitable. At a lower surrounding pressure as in a vein a higher liquid permeability would be more suitable.

By means of the present invention, a system for continuous measurement of substances in a pressurised body fluid without needing to provide a perfusion fluid to the probe is achieved. The system may be designed without pump, syringe, or perfusion fluid, and will therefore be less complex. Furthermore, the probe may be designed without an inlet channel for perfusion fluid, resulting in that the probe may be designed with smaller dimensions, or contain additional lumens and/or components.

Moreover, since no perfusion fluid needs to be provided, the spontaneous fluid flow from the probe to be analysed will not be diluted and will always exactly reflect the concentration in the body fluid.

Although particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made to the invention without departing from the spirit and scope of the invention as defined by the claims.

The invention is generally defined by the following independent claims.

The invention claimed is:

1. A probe adapted for insertion into an artery of a patient, comprising an essentially cylindrical elongated body having a proximal part, a distal part, and at least one chamber part at an outer cylindrical surface of the body and covered by a membrane, wherein the probe is provided with a single flow lumen, wherein the chamber part is in fluid connection with the flow lumen, and the flow lumen is operable to transport a spontaneous flow of fluid, continuously obtained from the artery through the membrane into the chamber part, from the distal part of the body to the proximal part of the body for subsequent measurement of the concentration of one or more substances present in the artery, wherein the membrane has a liquid permeability of about $5\text{-}50*10^{-4}$ cm/(bar*s).

2. A probe according to claim 1 devoid of any other flow lumen.

3. The probe according to claim 1, wherein the chamber part is in fluid connection with the flow lumen via at least one through-hole provided from the chamber part to the single flow lumen.

4. The probe according to claim 1 wherein the chamber part is essentially annular and covered by the membrane and wherein a single through-hole connects the chamber part with the single flow lumen.

5. A probe according to claim 1, wherein the membrane has a surface area of about 5-500 mm$^2$.

6. A probe according to claim 1, wherein the membrane has a thickness of 30-80 µm.

7. A probe according to claim 1, wherein the single flow lumen has an internal diameter of about 0.05-0.3 mm and the probe has a length of about 5-60 cm.

8. A probe according to claim 1, wherein the membrane has a surface area of 30-200 mm$^2$ and a thickness of 30-80 µm.

9. A probe according to claim 8 with a length of about 50-250 mm; an external diameter of about 0.7-1.4 mm; an internal flow lumen of about 0.1-0.3 mm; and a membrane of a hollow-fibre type having an outer diameter of about 0.9-1.6 mm, a wall thickness of about 30-80 µm, a surface area of about 30-100 mm$^2$ and a liquid permeability of about $20\text{-}50*10^{-4}$ cm/(bar*s).

10. A probe according to claim 1, wherein the probe is adapted for continuous measurement.

11. A probe according to claim 1, further comprising at least one additional lumen that provides direct access to the artery.

12. A self-flowing system for measuring the concentration of one or more substances in an artery, said system comprising:
   a) a probe according to claim 1; and
   b) a sensor adapted to receive the fluid and analyze said fluid, the sensor being connected to an outlet of the flow lumen.

13. A probe according to claim 1, comprising one or more inoperable flow lumens.

14. A probe according to claim 1, wherein the probe is adapted for collection of at least one sample.

15. A probe according to claim 1, wherein the membrane has a surface area of about 30-200 mm$^2$.

16. A probe according to claim 1, wherein the single flow lumen has an internal diameter of about 0.15 mm, and the probe has a length of about 5-60 cm.

17. A method of manufacturing a probe adapted for insertion into an artery, that ascertains a continuous fluid flow through a membrane contacting arterial blood and is provided with a flow lumen extending from a distal part of the probe to a proximal part of the probe for sampling or sensing of one more compounds in the arterial blood, comprising the steps of:
   a) providing an elongated probe body having an internal flow lumen connected to a chamber part, wherein the chamber part is at an outer cylindrical surface of the body and is coverable with a membrane;
   b) estimating at least one of the systolic pressure and the diastolic pressure in the artery in a selected body site;
   c) selecting a membrane which at the estimated arterial pressure provides a spontaneous fluid flow of about 1-50 μl/min in the single flow lumen following contact with the arterial blood; and
   d) attaching the membrane to sealingly cover the probe chamber part.

18. A method according to claim 17, comprising providing the elongated probe body with an internal single flow lumen and a single through-hole connecting the chamber part and the single flow lumen.

19. A method according to claim 17, comprising providing an elongated probe body with one or more additional inoperable internal flow lumens.

20. A method according to claim 17, wherein the membrane is selected from a kit of membranes, and wherein each membrane in the kit has a liquid permeability, area and thickness adapted to an arterial pressure or pressure range.

21. A method according to claim 17, wherein the selecting step comprises selecting a membrane which at the estimated arterial pressure provides a spontaneous fluid flow of about 2-10 μl/min in the single flow lumen following contact with the arterial blood.

22. A method according to claim 17, wherein the selecting step comprises selecting a membrane which at the estimated arterial pressure provides a spontaneous fluid flow of about 3-7 μl/min in the single flow lumen following contact with the arterial blood.

23. A method for measuring the concentration of one or more substances in an artery, comprising the steps of:
   a) inserting a probe according to claim 1 in an artery,
   b) establishing a spontaneous fluid flow through the membrane of the probe,
   c) transporting at least a part of said fluid flow to a sensor adjacent to a probe outlet, and
   d) continuously detecting a substance present in the artery.

24. A method according to claim 23, comprising establishing a spontaneous fluid flow through the membrane of about 1-50 μl/min.

25. A method according to claim 23, comprising establishing a spontaneous fluid flow through the membrane of about 2-10 μl/min.

* * * * *